United States Patent [19]
Sittinger et al.

[11] Patent Number: 5,932,459
[45] Date of Patent: Aug. 3, 1999

[54] ARTIFICIAL TISSUES, METHODS FOR THE PRODUCTION AND THE USE THEREOF

[76] Inventors: Michael Sittinger, Karl-Marx-Strasse 147D, D-15831 Grossziethen; Olaf Schultz, Steinstrasse 10, D-10119 Berlin; Gerd R. Burmester, Tullaweg 7, D-12277 Berlin; Thomas E. M. Häupl, Am Schützenwäldchen 59, D-15537 Erkner, all of Germany

[21] Appl. No.: 08/860,111

[22] PCT Filed: Oct. 18, 1996

[86] PCT No.: PCT/DE96/02025

§ 371 Date: Aug. 15, 1997

§ 102(e) Date: Aug. 15, 1997

[87] PCT Pub. No.: WO97/15655

PCT Pub. Date: May 1, 1997

[30] Foreign Application Priority Data

Oct. 20, 1995 [DE] Germany ............................ 195 40 487
Aug. 2, 1996 [DE] Germany ............................ 196 32 404

[51] Int. Cl.[6] ............................ C12N 11/08; C12N 5/06; C12N 5/00; A01N 1/02
[52] U.S. Cl. ...................... 435/180; 435/283.1; 435/347; 435/373; 435/382; 435/402
[58] Field of Search .................... 435/172.3, 325, 435/373, 384, 399, 320.1, 180, 283.1, 347, 382, 402; 514/44; 536/23.5

[56] References Cited

U.S. PATENT DOCUMENTS

| | | | |
|---|---|---|---|
| 5,478,739 | 12/1995 | Slivka et al. ............................. | 435/399 |
| 5,580,781 | 12/1996 | Naughton et al. ....................... | 435/1.1 |
| 5,627,021 | 5/1997 | Goodwin et al. ........................ | 435/1.1 |
| 5,712,161 | 1/1998 | Koezuka et al. ........................ | 435/382 |
| 5,736,372 | 4/1998 | Vacanti et al. .......................... | 435/180 |
| 5,741,685 | 4/1998 | Vacanti .................................... | 435/182 |

FOREIGN PATENT DOCUMENTS 0339607  11/1989  European Pat. Off. ....... A61K 35/34

OTHER PUBLICATIONS

J. Bonaventure, et al.; "Reexpression of Cartilage–specific Genes by De–differentiated Human Articular Chondrocytes Cultures in Alginate Beads"; *Exp. Cell Res. 1994,* 212(1), 97–104 (Eng).

*Primary Examiner*—James Ketter
*Assistant Examiner*—William Sandals
*Attorney, Agent, or Firm*—Londa and Traub LLP

[57] ABSTRACT

The invention relates to new artificial tissues which comprise three-dimensional extracellular matrixes (ECM) in cross-linkable structures, cell interaction systems for inducing artificial three-dimensional tissues and which comprise genetically manipulated cells releasing immunosuppressive or cell-differentiating factors. The tissues according to the invention are suitable for producing vital transplants and for establishing models of diseases.

9 Claims, 3 Drawing Sheets

ARTIFICIAL TISSUES, METHODS FOR THE PRODUCTION AND THE USE THEREOF

BACKGROUND OF THE INVENTION

The invention relates to new artificial tissues, methods for the production and the use thereof, and to cell interaction systems for inducing artificial tissues for the purpose of producing vital transplants and establishing models of diseases. Such cell interaction culture systems for in vitro organ and tissue models are suitable for producing three-dimensional cell tissues using three-dimensional supporting structures which permit formation of an extracellular matrix (ECM) but initially, do not have any ECM themselves. The close interaction of artificial tissues permits setting up models of diseases where cell and matrix changes by external effects, e.g., by administration of medicaments, can be tested in boundary zones.

Numerous cell culture systems are known, wherein an extracellular matrix (ECM) has been described. Thus, the patent specification DE 3,410,631 presents an implantation material for repairing defective cartilage and bones, which either is in the form of a gel or embedded in natural or artificial bone material. The gel includes embryonic species-specific chondrocytes or mesenchyme cells and preferably also an extracellular matrix of chondrocytes and growth hormones. U.S. Pat. No. 4,801,299 (U.S. patent specification) suggests body implants in the form of an extracellular matrix based on collagen.

U.S. Pat. No. 4,935,000 is directed to a method for tissue regeneration using extracellular matrix induction. In addition, extracellular matrices are also used in context with human skin regeneration, cosmetic compositions (U.S. Pat. No. 5,055,298) and, on collagen or fibronectin basis, for attaching T-cells (U.S. Pat. Nos. 5,188,959 and 5,354,686). DE 4,336,399 describes collagen (type 1) as base matrix for the stationary phase of bipolar-adhered cell culture hepatocytes.

The DE 4,323,487 is directed to the functional immobilization of enzymes, proteins and whole cells on solid, biocompatible support materials by means of electrostatic interaction between the surface coating of the solid and the adsorbate to be fixed. WO 92/20780 (DE 4,116,727) describes the simultaneous cultivation of various mammalian cells, the separate production of various mammalian cell products and the modelling of organ interactions on a humoral level.

In the production of implants, methods have become familiar starting from bundles of polymeric fiber made of an absorbable material, onto which the isolated and grown cells are applied and the bundles are implanted. WO 90/12603 reports three-dimensional supporting structures formed in the shape of the organ to be replaced and added with the desired cells. In three-dimensional supporting structures, however, there is the problem of providing sufficient nutrients for the cells in the interior of the implant.

DE 4,306,661 claims the production of implants from cell cultures. Therein, cartilage cells are applied onto an absorbable, pre-formed, three-dimensional supporting structure corresponding to the desired structure of the implant, and the structure is enveloped with a material allowing a nutrient solution to diffuse therethrough. In this way, an intercellular matrix may be formed by mutual binding of cells. During and after a transplantation, the artificially produced cartilage tissue is exposed to a number of negative effects jeopardizing long-term stability of the tissue (Buja J. et al., Ann. Rheum. Dis. 1994 Apr. 53(4), 229–34). For example, this is particularly important in patients suffering from arthrosis or rheumatoid arthritis. Here, the implanted tissue must have a local effect against pathologically degenerative and inflammatory processes.

Several methods for producing transplantable cartilage-replacing tissue are known (Vacanti C. A. et al., Plastic and Reconstructive Surgery, 8, 753–759, 1991; Sittinger M. et al., Biomaterials 1994, 15, 451–456).

Also, ways have been described to provide cells of the joint interior skin with predominantly anti-inflammatory genes ex vivo and to re-implant them (Evans C. H. and P. D. Robbins, 1994: Gene Therapy for Arthritis, in Gene Therapeutics: Methods and Applications of Direct Gene Transfer; J. A. Wolff, editor, Birkhäuser, Boston, 312–343).

SUMMARY OF THE INVENTION

The invention is based on the object of providing new artificial tissues, developing methods for their production, and enabling their use in medicine.

The object of the invention is attained by providing new artificial interacting tissues consisting of new three-dimensional extracellular matrices (ECM) in crosslinkable structures, cell interaction systems for inducing artificial three-dimensional tissues, and genetically manipulated cells releasing immunosuppressive or cell-differentiating factors.

According to the invention, cell interaction systems for inducing artificial three-dimensional tissues are employed in such fashion that cultures possessing or developing an extracellular matrix are linked to each other via membranes, or are in direct contact with each other, or are mixed with each other. Thus, induction of an artificial cell tissue to give cartilage or bone tissue, for example, is effected by transfected cell cultures or three-dimensional cultures of periosteal or perichondrial cells. The object of achieving transplant stabilization was attained by genetic manipulation of cells, particularly by providing human cells with specific genes, e.g., bone morphogenic protein, interleukin-1 receptor antagonist, or TGF-β, and subsequently, cultivating them to give new cartilage tissue.

DETAILED DESCRIPTION OF THE INVENTION

Figure 1:
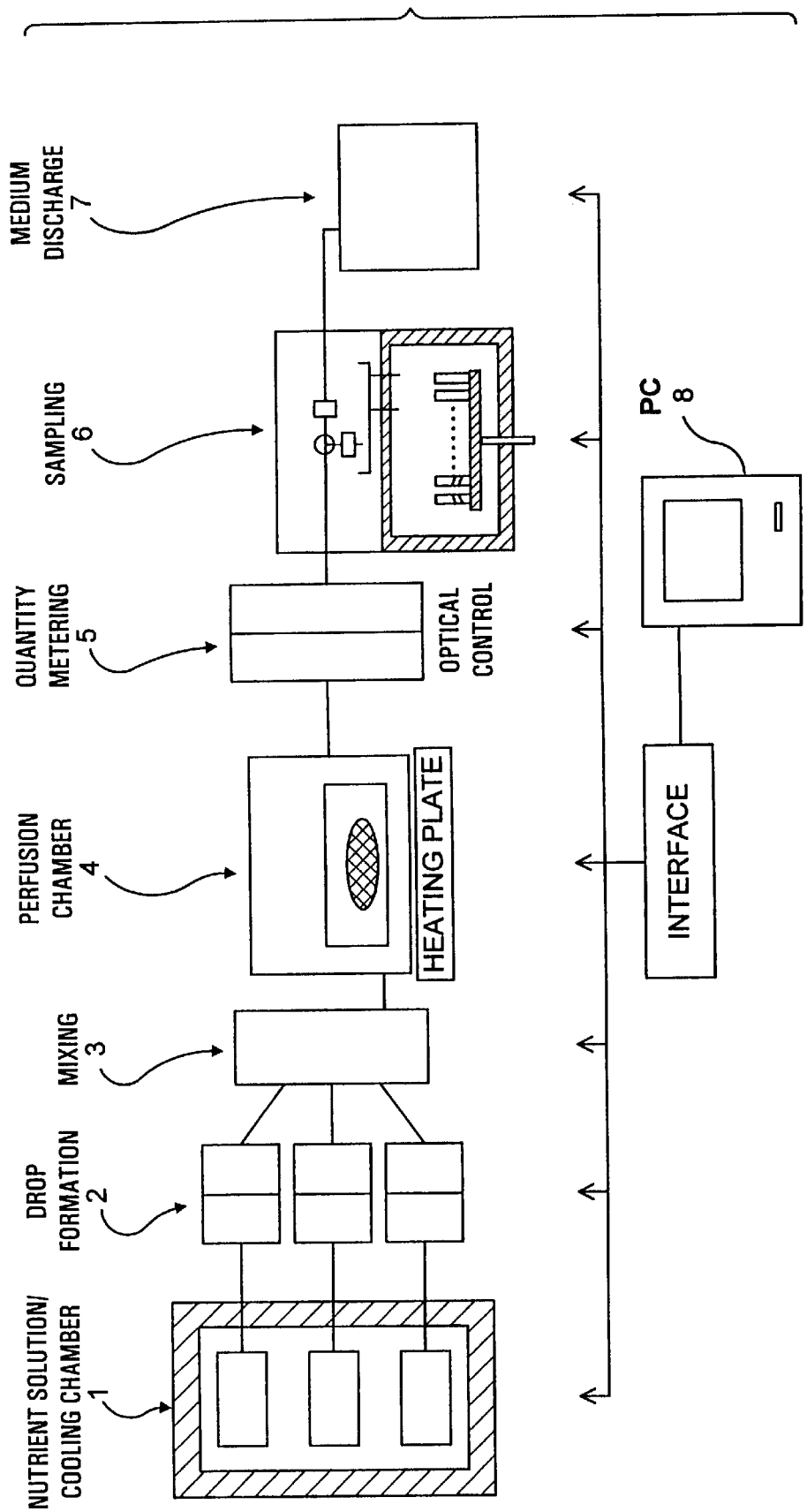
FIG. 1 is a schematic diagram showing a cell interaction system of the invention.

The invention consists in a combination of new and well-known elements co-operating in such a way as to form products having new and improved properties. The cell interaction system of the invention (FIG. 1) consists of a nutrient solution/cooling tank 1, a drop formation chamber 2, a mixing chamber 3, a perfusion chamber 4 (with heating plate), a quantity metering unit 5 (optical control), a sampling unit 6, a medium discharge chamber 7, and an interface/PC 8. According to the invention, the three-dimensional cell tissues are produced using three-dimensional supporting structures, e.g., absorbable polymer fleeces. For example, disdifferentiated (grown) cartilage cells or non-differentiated mesenchymal precursor cells are used to produce cartilage tissue. In general, differentiated cartilage cells from a patient are available only in minor amounts (operative procedure necessary).

In order to generate a differentiating micromedium, a) a non-differentiated cell suspension is mixed with endogenous cells or cell aggregates of a defined (differentiated) phenotype, b) defined (e.g., differentiated) or genetically manipulated exogenous cells are suspended in a gel or fleece and placed around the tissue or directly on the tissue to be differentiated.

The design of this process produces a defined contact zone between two artificial three-dimensional cell tissues. Said contact zone serves as a testing system for diseases. Cell and matrix changes, e.g., when administering medicaments, may be tested in the boundary zones.

The interacting cell culture systems of the invention are suitable for use as in vitro organ and tissue models.

Surprisingly, it was found that, e.g., the induction of an artificial cell tissue by transfected cell cultures or three-dimensional cultures of periosteal or perichondrial cells developing or possessing an extracellular matrix to yield cartilage or bone tissue permits setting up models of diseases where, in particular, the extracellular matrix is of importance. The use of these new interacting artificial tissues consists in the production of vital transplants suitable for in vitro simulation of pathogenetic and infectious processes, for establishing models of diseases, and for testing active substances.

Figure 2:
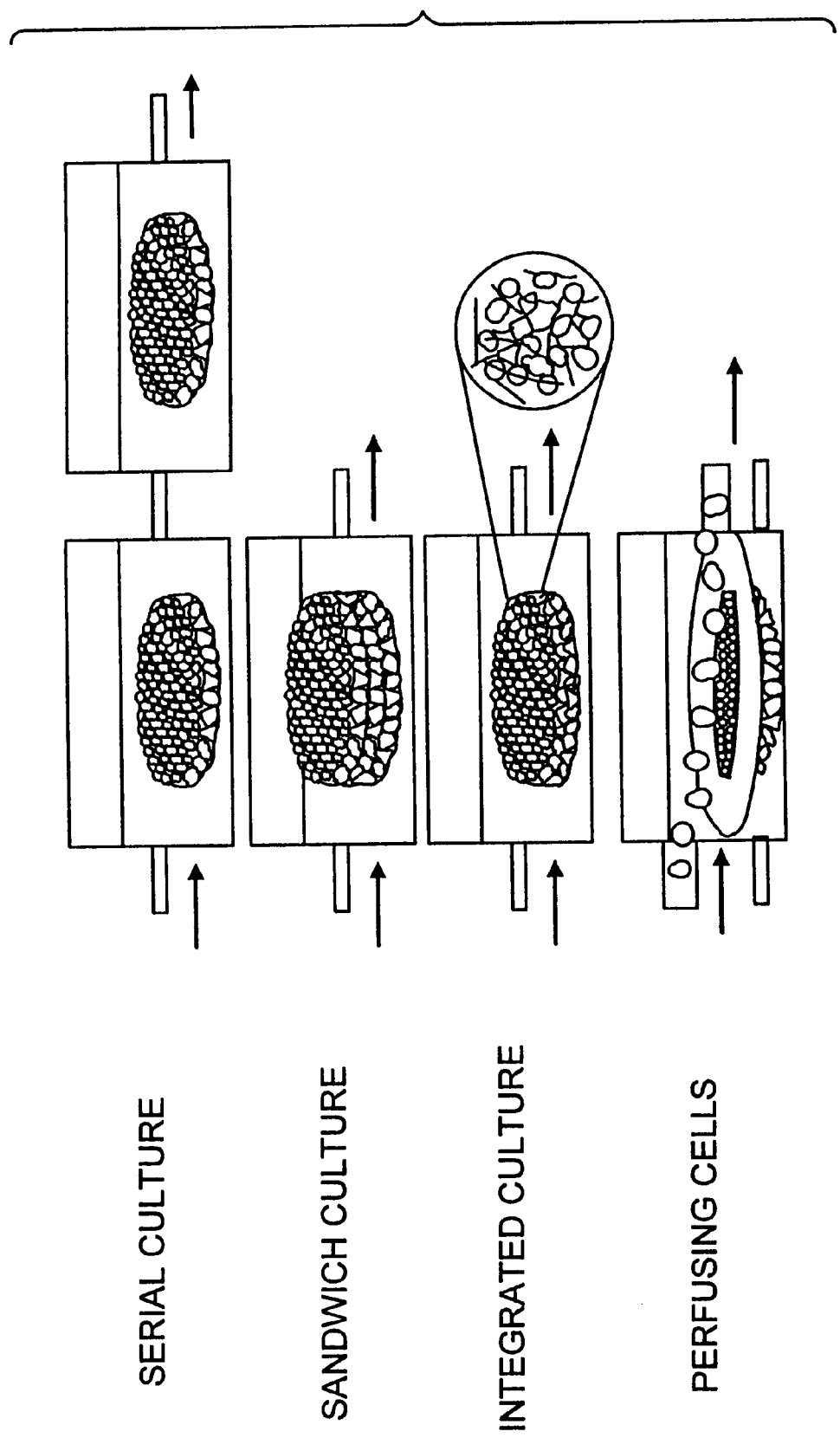
FIG. 2 depicts schematic arrangements of various cell and tissue arrangements.
Figure 3:
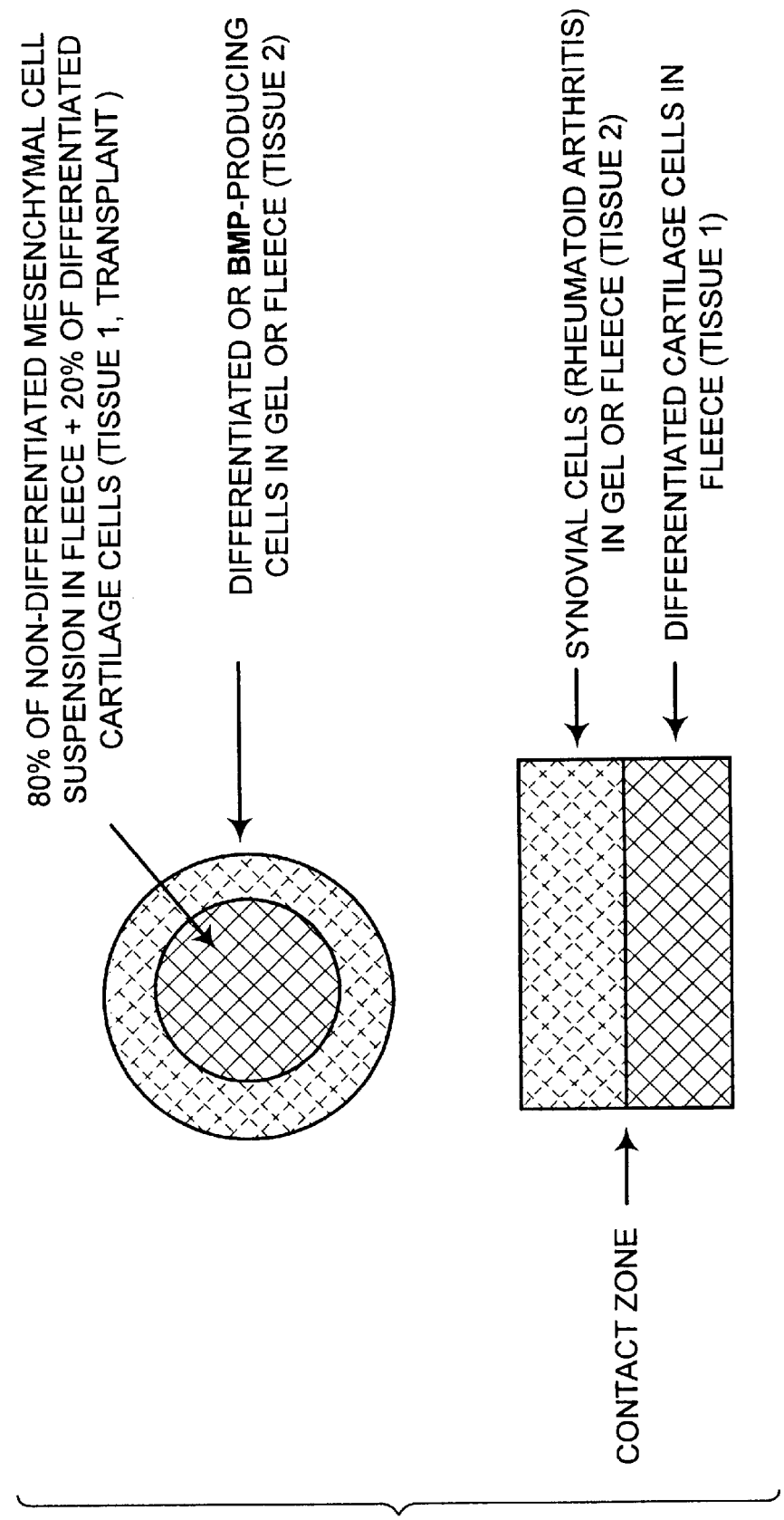
FIG. 3 depicts cell differentiation in schematic fashion.

FIG. 2 shows cell and tissue arrangements:

Serial culture: Factors from the tissue (left) act upon the right tissue. The factor from the right tissue does not act upon the left tissue.

Sandwich culture: Two or more artificial tissues are superposed or adjacent (contact zones).

Integrated culture: This is a mixture of different cells for the purpose of tissue differentiating.

Perfusing cells: Suspended cells in admixture (e.g., lymphocytes or micro-organisms as well) flow along an artificial tissue (e.g., endothelium) and attach thereto if the cells express appropriate receptors.

FIG. 3:

Upper picture: The purpose of cell mixing is to differentiate as many non-differentiated cells as possible, using the few differentiated or differentiating cells. 80% of the non-differentiated mesenchymal cells and 20% of the differentiated cartilage cells are together in one tissue (tissue 1). When producing differentiating factors, exogenous or genetically manipulated cells are arranged around tissue 1.

Lower picture (contact zone): In rheumatoid arthritis, synovial cells destroy the joint cartilage in the joints of patients by destroying its surface and extracellular matrix and eventually, synovial cells penetrate the cartilage.

The transplantable cartilage tissues stabilized according to the invention consist of a new extracellular matrix (ECM) in three-dimensional structures, grown cartilage cells, crosslinkable/polymerizable polypeptides or polysaccharides, and cells releasing matrix molecules, immunosuppressive or cell-differentiating factors due to genetic manipulation. Their structures are composed of three-dimensional fiber structures, three-dimensional tissues, fibrin, and a semipermeable membrane surrounding the artificial cartilage system.

For example, a desirable form is composed of a silicone negative, fiber wool or fiber structures made of absorbable polymers such as α-hydroxy acids, and the semipermeable membrane is composed of polyelectrolyte complexes such as polylysine or hyaluronic acid.

The methods of producing transplantable cartilage tissue consist in filling cartilage cell suspensions containing polymerizable solutions, and gene-therapeutically modified cells into three-dimensional structures, solidifying them using thrombin or factors inducing polymerization, the cells within said three-dimensional structure producing a new extracellular matrix (ECM), and surrounding the cartilage system with a semipermeable membrane.

The polymerizable solutions consist of crosslinkable/polymerizable polypeptides or polysaccharides, and the modified cells consist of those which, due to genetic manipulation, release matrix molecules, immunosuppressive or cell-differentiating factors.

Fibrinogen is used as polypeptide in such a way that cell suspensions containing fibrinogen are filled into structures made of three-dimensional fiber structures or three-dimensional tissues and are solidified using thrombin.

The fibrinogen is recovered from that patient from whom the cells are derived and/or into whom the three-dimensional cartilage tissue is to be implanted.

According to the invention, all or part of the cells are gene-therapeutically modified using one or more of the following genes: TGF-β, bone morphogenetic proteins, morphogenes, receptors for morphogenes, anti-inflammatory cytokines, cytokine antagonists such as IL-1 antagonists, IL-1 receptor antagonists, TNF antagonists, or using protease inhibitors (TIMP, PAI).

Here, different cells each having just one genetic manipulation or multiple cells having different genetic manipulations may be combined with non-modified cells. The incorporated genes are expressed temporarily or permanently. Surprisingly, shaping and genetic manipulation may be employed to achieve a polarization based on an uneven distribution of genetically manipulated cells and non-modified cells.

Another feature of the invention is that genetically manipulated and non-modified cells are incorporated in separate artificial tissues, shaped and combined to a complete tissue, or shaped tissues are combined with genetically manipulated cells and non-modified cells in layers or by enveloping, or two or multiple tissues each having different genetic manipulations are combined in layers or by enveloping.

Tissues containing genetically manipulated cells may be combined with tissues containing genetically non-modified cells.

In particular, the cartilage tissues produced according to the invention have immunosuppressive properties.

Surprisingly, it was found that the procedure according to the invention is suitable for in vivo protection and in vivo maintenance of cartilage produced in vitro, and that the cartilage tissues of the invention may be used in the therapy of patients having rheumatoid arthritis. It is also surprising that the semipermeable membrane used according to the invention, by which the produced cartilage tissues are surrounded prior to, during and some time after implantation, offer protection against immunological and disdifferentiating reactivities.

The invention will be illustrated in more detail by reference to the embodiments.

EMBODIMENTS

Example 1

Three-dimensional Cell Tissue

A three-dimensional cell tissue is produced using three-dimensional supporting structures (absorbable polymer fleece). For producing a cartilage tissue, a) disdifferentiated (grown) cartilage cells or b) non-differentiated mesenchymal precursor cells are used. Initially, the cells to be distributed within the fleece structure are suspended in a fibrinogen solution. The cell suspension is filled into the fleece support and solidified by thrombin addition.

Example 2

Differentiating Micromedium

In order to generate a differentiating micromedium, (A) a non-differentiated cell suspension is mixed 5:1 with endogenous cells or cell aggregates of a differentiated phenotype, (B) differentiated—though exogenic—cells are suspended in a gel or a polymer fleece and attached around or directly to the tissue to be differentiated.

The differentiating micromedium may be generated using 1. differentiated cartilage cells,
2. cells transfected with BMP (bone morphogenetic protein)
3. all the cells (periosteal and perichondrial cells), tissues (periosteum, synovia) or tissue components (matrix) producing or releasing cartilage-differentiating factors in a paracrine fashion.

Currently known factors are, e.g., bone morphogenetic proteins, cartilage derived morphogenetic proteins, transforming growth factor beta (Luyten F. P. et al., Acta Orthop. Belg., 58, Suppl. 1 (1992) 263–267; Exp. Cell Res. 1994, 210, 224–9; Chang S. C. et al., J. Biol. Chem. 1994, 269, 28227–28234).

Example 3

The Rheumatoid Arthritis Model

Aggressive cells from the synovia of a patient having rheumatoid arthritis (3D tissue 1) invade the cartilage cell tissue (3D tissue 2) in vitro.

Example 4

Cartilage Tissue

Grown cartilage cells or mesenchymal precursor cells having various degrees of maturing and differentiation are suspended in a fibrinogen solution, the cell suspension is distributed within an absorbable polymer fleece, factors or components of the appropriate extracellular matrix, which promote the process of growing and differentiating, are added and solidified by thrombin addition and exposed to a differentiating micromedium.

Example 5

Bone Tissue

Cells of osteogenic origin having various degrees of maturing and differentiation or mesenchymal precursor cells are suspended in a fibrinogen solution, the cell suspension is distributed within an absorbable polymer structure, factors or components of the appropriate extracellular matrix, which promote the process of growing and differentiating, are added and solidified by thrombin addition and exposed to a differentiating micromedium.

Example 6

The "Rheumatoid Arthritis/In vitro Pannus Tissue" Model

As in Example 3, synovial membrane cells of a patient having rheumatoid arthritis (3D tissue 1) interact with cartilage cell tissue (3D tissue 2) in vitro.

Example 7

Transplantation of Artificially Produced Cartilage Tissue for the Therapy of Cartilage Lesions in Rheumatoid Arthritis Patients Mesenchymal cells from a tissue sample of a patient are grown sufficiently in a monolayer culture and transfected partially with a BMP (bone morphogenetic protein) gene. The cells are suspended in a solution containing fibrinogen and then are placed in a supporting structure (e.g., absorbable polymer fleeces made of polylactide and polyglycolide). The suspension is then solidified in its structure by adding thrombin. The tissue may be transplanted into the patient's joint immediately or after in vitro maturing.

Example 8

Other Artificial Tissues—Bone, Liver, Kidney, Skin

Comparable to Example 1, part of the cells are manipulated with a desired gene, and the gene-therapeutically modified population is formed into a specific shape using supporting structures and fibrin. Likewise using shaping structures, genetically non-modified cells are then attached to said structure, so that a diffusion gradient and thus, an activity gradient for genetically incorporated active substances may act upon the non-treated cells. This serves to polarize the tissue structures produced in vitro, comparable to the polarization in the native joint cartilage.

We claim:

1. A method of producing new artificial tissues using cell interaction systems to establish a rheumatoid arthritis/in vitro-pannus tissue model, comprising the steps of:

preparing a first cell culture system, comprising the steps of:
suspending synovial membrane cells of a patient having rheumatoid arthritis, to form a suspension in a solution which can be induced to polymerize,
applying factors or components which promote the process of differentiation and tissue formation of said cells, and
adding an inducer of polymerization to effect solidification thereof;

preparing at least one second cell culture system, comprising the steps of:
suspending cartilage cell tissue in vitro for inducing differentiation of the cells of the first cell culture systems, to form a suspension in a solution which can be induced to polymerize, and
adding an inducer of polymerization to effect solidification thereof;

distributing, prior to the step of adding an inducer of polymerization, either one or both of the suspension of the first cell culture system and the suspension of the second cell culture system within an absorbable polymer fleece; and contacting said first cell culture system with said second cell culture system.

2. The method of claim 1, wherein prior to distributing within the polymer fleece, the contacting step is effected by homogeneous mixing of the first and second cell culture systems.

3. The method of claim 1, wherein, prior to the solidification step, either one or both of the first and second cell culture systems is placed in a mold.

4. The method of claim 1, wherein either one or both of the first and second cell culture systems, either individually or together, are encapsulated by a semipermeable membrane.

5. The method of claim 1, wherein one or more chosen from the group consisting of cells in the first cell culture system, genetically manipulated cells in the second cell culture system, and fibrin used as the inducer of polymerization, are of autologous origin.

6. The method of claim 1, wherein the solution which can be induced to polymerize, in either or both of the first and second cell culture sytems, comprises polypeptides or polysaccharides.

7. The method of claim 1, wherein the contacting step takes place after solidification of at least one of the first and second cell culture systems, to thereby take place across a boundary formed therebetween.

8. The method of claim 7, wherein the first cell culture system and the at least one second cell culture system are contacted in the form of one or both of layers, and an enveloping of one culture about another.

9. A method of producing new artificial tissues using cell interaction systems, comprising the steps of:

preparing a first cell culture system, comprising the steps of:

suspending cells chosen from one or more of the group consisting of differentiated, dedifferentiated and undifferentiated cells, to form a suspension in a solution which can be induced to polymerize, applying factors or components which promote the process of differentiation and tissue formation of said cells, and adding an inducer of polymerization to effect solidification thereof;

preparing at least one second cell culture system, comprising the steps of:

suspending a means for inducing differentiation of the cells of the first cell culture systems, said means consisting of one or more chosen from the group consisting of differentiated cells, cells producing factors of differentiation and genetically altered cells, to form a suspension in a solution which can be induced to polymerize, and adding an inducer of polymerization to effect solidification thereof;

distributing, prior to the step of adding an inducer of polymerization, either one or both of the suspension of the first cell culture system and the suspension of the second cell culture system within an absorbable polymer fleece; and contacting said first cell culture system with said second cell culture system, wherein the method takes place in a unit comprising a nutrient solution/cooling tank, a drop formation chamber, a mixing chamber, a perfusion chamber with heating plate, a quantity metering unit, a sampling unit, a medium discharge chamber, and an interface/computer.

* * * * *